United States Patent
Cottard et al.

(10) Patent No.: US 7,198,649 B2
(45) Date of Patent: Apr. 3, 2007

(54) OXIDATION DYEING COMPOSITION FOR KERATINOUS FIBERS COMPRISING GLYCERINE AND A POLYOL OTHER THAN GLYCERINE IN A SPECIFIC RATIO

(75) Inventors: Francois Cottard, Courbevoie (FR); Christine Rondeau, Sartrouville (FR)

(73) Assignee: L'Oreal, Paris (FR)

( * ) Notice: Subject to any disclaimer, the term of this patent is extended or adjusted under 35 U.S.C. 154(b) by 154 days.

(21) Appl. No.: 10/432,603

(22) PCT Filed: Nov. 22, 2001

(86) PCT No.: PCT/FR01/03692

§ 371 (c)(1),
(2), (4) Date: Sep. 25, 2003

(87) PCT Pub. No.: WO02/45673

PCT Pub. Date: Jun. 13, 2002

(65) Prior Publication Data

US 2004/0049860 A1    Mar. 18, 2004

(30) Foreign Application Priority Data

Dec. 4, 2000    (FR) .................................. 00 15683

(51) Int. Cl.
*A61K 7/13*    (2006.01)
(52) U.S. Cl. ..................... 8/405; 8/410; 8/411; 8/421; 8/425; 8/552; 8/611
(58) Field of Classification Search ................. 8/405, 8/410, 411, 421, 425, 552, 554, 611
See application file for complete search history.

(56) References Cited

U.S. PATENT DOCUMENTS 4,719,099 A * 1/1988 Grollier et al. ............... 424/47
6,156,076 A * 12/2000 Casperson et al. ............ 8/406

FOREIGN PATENT DOCUMENTS

| DE | 40 05 008 | 8/1991 |
| EP | 0 351 645 | 1/1990 |
| JP | H8-268848 | 10/1996 |
| JP | H10-287534 | 10/1998 |
| JP | 2001-240520 | 9/2001 |
| JP | 2001-328926 | 11/2001 |
| WO | 98 27942 | 7/1998 |

OTHER PUBLICATIONS

Observation re: Japanese Application No. 2002-547459 to Commisioner, Japanese Patent Office, Mar. 23, 2005, pp. 1-7.

* cited by examiner

*Primary Examiner*—Eisa Elhilo
(74) *Attorney, Agent, or Firm*—Oblon, Spivak, McClelland, Maier & Neustadt, P.C.

(57) ABSTRACT

The invention concerns a composition for dyeing keratinous fibres, in particular human keratinous fibres and more particularly hair, comprising, in a medium suitable for dyeing, at least an oxidation dye, at least a C12–C30 fatty alcohol, at least an oxyalkylene or polyglycerol C12–C30 fatty alcohol and further 2 to 15 wt. % and preferably 5 to 10 wt. % of a mixture of glycerine (A) and a polyol other than glycerine (B) in an (A)/(B) weight ratio >1. The invention also concerns dyeing methods and devices using said composition.

41 Claims, No Drawings

OXIDATION DYEING COMPOSITION FOR KERATINOUS FIBERS COMPRISING GLYCERINE AND A POLYOL OTHER THAN GLYCERINE IN A SPECIFIC RATIO

The invention relates to a composition intended for the oxidation dyeing of keratinous fibers, in particular human keratinous fibers, and more particularly hair, comprising, in an appropriate medium for dyeing, at least one oxidation dye, at least one $C_{12}$–$C_{30}$ fatty alcohol and at least one oxyalkylenated or polyglycerolated $C_{12}$–$C_{30}$ fatty alcohol and additionally 2 to 15% by weight, and preferably 5 to 10% by weight, of a mixture of glycerine (A) and a polyol different than glycerine (B) in an (A)/(B) weight ratio >1.

The invention also relates to the dyeing methods and devices using said composition.

In the hair domain, it is possible to distinguish two types of dyeing.

The first is semipermanent or temporary dyeing, or direct dyeing, which involves dyes capable of giving the natural coloration of the hair a more or less marked color modification which is possibly resistant to several shampooings. These dyes are called direct dyes.

The second is permanent dyeing or oxidation dyeing. The latter is carried out with so-called "oxidation" dyes comprising oxidation dye precursors and couplers. The oxidation dye precursors, commonly called "oxidation bases", are compounds which are initially colorless or faintly colored which develop their dyeing power inside the hair in the presence of oxidizing agents added at the time of use, leading to the formation of colored and dyeing compounds. The formation of these colored and dyeing compounds results either from an oxidative condensation of the "oxidation bases" with themselves, or from an oxidative condensation of the "oxidation bases" with color modifying compounds commonly called "couplers" and generally present in the dyeing compositions used in oxidation dyeing.

The variety of molecules used, which consist, on the one hand, of the oxidation bases and, on the other hand, of the couplers, makes it possible to obtain a very rich palette of colors.

To further vary the shades obtained with said oxidation dyes, or to increase their glint, direct dyes are sometimes added to them.

The so-called "permanent" dyeing obtained using these oxidation dyes should moreover satisfy a number of requirements. Thus it should make it possible to obtain shades in the desired intensity and should exhibit good resistance to external agents (light, adverse weather conditions, washing, permanent waving, perspiration, rubbing).

The dyes should also make it possible to cover gray hair, and should finally be the least selective possible, that is to say they should make it possible to obtain the smallest possible differences in coloration all along the same keratinous fiber, which may indeed be differently sensitized (i.e. damaged) between its tip and its root.

The compositions which contain the oxidation dyes and which, once mixed with an oxidizing agent, are applied to the fibers in order to obtain said oxidation dye described above, often contain fatty alcohols. These fatty alcohols make it possible to thicken the dyeing media but have the disadvantage of slowing the rise of the dyes on the fiber; moreover, they can be irritating for the scalp and the dyeing compositions containing them are not always very stable.

The applicant has now discovered, quite unexpectedly and surprisingly, novel compositions containing oxidation dyes which are therefore free of oxidizing agent (and which will be called, for the purposes of the present invention, dye compositions), based on fatty alcohols, intended to be mixed with an oxidizing agent in order to be able to dye the keratinous fibers by a so-called oxidation dyeing method and which have the advantage of being stable and nonirritating; these dye compositions do not slow the rise of the dyes on the fibers and consequently make it possible to obtain intense shades by oxidation. This discovery forms the basis of the present invention.

The subject of the present invention is thus a novel composition for the oxidation dyeing of keratinous fibers, in particular human keratinous fibers, and more particularly hair, comprising, in an appropriate medium for dyeing, at least one oxidation dye, at least one $C_{12}$–$C_{30}$ fatty alcohol and at least one oxyalkylenated or polyglycerolated $C_{12}$–$C_{30}$ fatty alcohol and which is characterized in that it additionally contains 2 to 15% by weight, and preferably 5 to 10% by weight of a mixture of glycerine (A) and of a polyol different from glycerine (B) in an (A)/(B) weight ratio >1.

The invention also relates to a method for dyeing keratinous fibers, in particular human keratinous fibers and more particularly hair, consisting in applying to the fibers at least one dye composition comprising, in an appropriate medium for dyeing, at least one oxidation dye, at least one $C_{12}$–$C_{30}$ fatty alcohol and at least one oxyalkylenated or polyglycerolated $C_{12}$–$C_{30}$ fatty alcohol and in addition 2 to 15% by weight of a mixture of glycerine (A) and a polyol different from glycerine (B) in an (A)/(B) weight ratio >1, the color being developed at alkaline, neutral or acidic pH, using an oxidizing composition containing at least one oxidizing agent which is mixed just at the time of use with the dye composition or which is sequentially applied without intermediate rinsing.

The subject of the invention is also a two-compartment device with a first compartment containing a dye composition comprising, in an appropriate medium for dyeing, at least one oxidation dye, at least one $C_{12}$–$C_{30}$ fatty alcohol and at least one oxyalkylenated or polyglycerolated $C_{12}$–$C_{30}$ fatty alcohol and in addition 2 to 15% by weight of a mixture of glycerine (A) and a polyol different from glycerine (B) in an (A)/(B) weight ratio >1, and a second compartment containing an oxidizing composition comprising, in an appropriate medium for dyeing, at least one oxidizing agent.

However, other characteristics, aspects, subjects and advantages of the invention will emerge even more clearly on reading the description and the examples which follow.

$C_{12}$–$C_{30}$ Fatty Alcohols and Oxyalkylenated or Polyglycerolated $C_{12}$–$C_{30}$ Fatty Alcohols The expression $C_{12}$–$C_{30}$ fatty alcohols is understood to mean any saturated or unsaturated, branched or unbranched pure fatty alcohol having from 12 to 30 carbon atoms or mixtures thereof.

By way of example of fatty alcohols according to the invention, there may be mentioned, for example, cetyl alcohol, oleyl alcohol, stearyl alcohol, cetylstearyl alcohol, behenyl alcohol or erucyl alcohol.

There may also be mentioned the commercial products NAFOL 18-22®, NAFOL 18-22B®, NAFOL 18-22 C®, NAFOL 20+®, NAFOL 20-22®, NACOL 22-98® from the company CONDEA, CRODACID PG 3220® from the company CRODA, EDENOR U 122® from the company HENKEL.

The $C_{12}$–$C_{30}$ fatty alcohols represent, by weight, from 0.1 to 15% approximately, preferably from 0.5 to 10% approximately, of the total weight of the composition.

The expression oxyalkylenated or polyglycerolated $C_{12}$–$C_{30}$ fatty alcohol is understood to mean any oxyalkylenated or polyglycerolated, saturated or unsaturated, linear or branched, pure fatty alcohol in which the number of ethylene oxide or propylene oxide groups is between 2 and 100, and the number of glycerol groups is between 1 and 30, and preferably between 1 and 10, or mixtures thereof.

Particularly preferred oxyalkylenated $C_{12}$–$C_{30}$ fatty alcohols according to the invention are saturated or unsaturated, linear or branched fatty alcohols containing 2 to 40 ethylene oxide groups.

As oxyalkylenated fatty alcohols, there may be mentioned in particular the following commercial products:
Mergital LM2® (COGNIS) [lauryl alcohol 2 EO];
Ifralan L12® (IFRACHEM) and Rewopal 12® (GOLDSCHMIDT) [lauryl alcohol 12 EO];
Brij 58® (UNIQUEMA) and Simulsol 58® (SEPPIC) [cetyl alcohol 20 EO];
Eumulgin O5 (COGNIS) [oleocetyl alcohol 5 EO];
Mergital OC30® (COGNIS) [oleocetyl alcohol 30 EO];
Brij 72® (UNIQUEMA) [stearyl alcohol 2 EO];
Brij 76® (UNIQUEMA) [stearyl alcohol 10 EO];
Brij 78P® (UNIQUEMA) [stearyl alcohol 20 EO];
Brij 700® (UNIQUEMA) [stearyl alcohol 100 EO];
Eumulgin B1® (COGNIS) [cetylstearyl alcohol 12 EO];
Eumulgin L® (COGNIS) [cetyl alcohol 9 EO and 2 PO];
Witconol APM® (GOLDSCHMIDT) [myristyl alcohol 3 PO].

As polyglycerolated fatty alcohols, there may be mentioned in particular lauryl alcohol containing 4 mol of glycerol (INCI name: POLYGLYCERYL4 LAURYL ETHER), oleyl alcohol containing 4 mol of glycerol (INCI name: POLYGLYCERYL-4 OLEYL ETHER), oleyl alcohol containing 2 mol of glycerol (INCI name: POLYGLYCERYL-2 OLEYL ETHER), cetearyl alcohol containing 2 mol of glycerol, cetearyl alcohol containing 6 mol of glycerol, oleocetyl alcohol containing 6 mol of glycerol, and octadecanol containing 6 mol of glycerol.

Several species of oxyalkylenated or polyglycerolated fatty alcohols can coexist in the form of a mixture in a commercial product.

The oxyalkylenated or polyglycerolated fatty alcohols represent, by weight, from 0.1 to 15% approximately, preferably from 0.5 to 10% approximately, of the total weight of the composition.

Polyols Different from Glycerine

The expression polyol denotes, for the purposes of the invention, saturated or unsaturated, linear, cyclic or branched $C_3$–$C_{10}$ hydrocarbon chains carrying at least two —OH functional groups on the chain, and polyalkylene glycols.

For the branched or unbranched αωdiols, [αω is, in the case of branched compounds, in relation to the longest carbon chain], there may be mentioned for example 1,3-propanediol; 1,4-butanediol; 1,5-pentanediol; 1,6-hexanediol; neopentyl glycol (or 2,3-dimethyl-1,3-propanediol).

Among the branched or unbranched 1,2-1,4-1,5-2,3-2,4-2,5-2,6-2,7-2,8-3,4-3,5-3,6 diols, there may be mentioned 2,5-hexanediol, 2,4-pentanediol (or amylene glycol); 2-methyl-2,4-pentanediol (or hexylene glycol); 2,3-dimethyl-2,3-butanediol (or pinacol).

Among the triols, there may be mentioned in particular 1,2,4-butanetriol and 1,2,6-hexanetriol.

Among the polyalkylene glycols, there may be mentioned diethylene glycol, dipropylene glycol and polyethylene glycols.

According to the present invention, the use of a diol is preferred, of which hexylene glycol is most particularly preferred.

In the dye compositions according to the invention, the glycerine represents from 1.5 to 14% by weight approximately of the total weight of the composition and the polyol(s) different from glycerine represent from 0.5 to 7% by weight approximately of the total weight of the composition.

The oxidation dyes which can be used according to the invention are chosen from oxidation bases and/or couplers.

Preferably, the compositions according to the invention contain at least one oxidation base.

The nature of these oxidation bases is not critical. They may in particular be chosen from ortho- and para-phenylenediamines, double bases, ortho- and para-aminophenols, the following heterocyclic bases as well as the addition salts of all these compounds with an acid.

There May be Mentioned in Particular:
(I) the para-phenylenediamines of the following formula (I) and their addition salts with an acid:

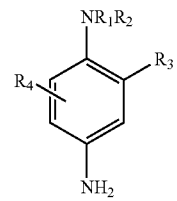

in which:
$R_1$ represents a hydrogen atom, a $C_1$–$C_4$ alkyl radical, a monohydroxy($C_1$–$C_4$ alkyl) radical, a polyhydroxy($C_2$–$C_4$ alkyl) radical, a ($C_1$–$C_4$)alkoxy($C_1$–$C_4$)alkyl radical, a $C_1$–$C_4$ alkyl radical substituted with a nitrogen-containing group, a phenyl radical or a 4'-aminophenyl radical;
$R_2$ represents a hydrogen atom, a $C_1$–$C_4$ alkyl radical, a monohydroxy($C_1$–$C_4$ alkyl) radical or a polyhydroxy ($C_2$–$C_4$ alkyl) radical, a ($C_1$–$C_4$)alkoxy($C_1$–$C_4$)alkyl radical or a $C_1$–$C_4$ alkyl radical substituted with a nitrogen-containing group;
$R_1$ and $R_2$ may also form with the nitrogen atom carrying them a 5- or 6-membered nitrogen-containing heterocycle optionally substituted with one or more alkyl, hydroxyl or ureido groups;
$R_3$ represents a hydrogen atom, a halogen atom such as a chlorine atom, a $C_1$–$C_4$ alkyl radical, a sulfo radical, a carboxyl radical, a monohydroxy($C_1$–$C_4$ alkyl) radical or a hydroxy($C_1$–$C_4$ alkoxy) radical, an acetylamino($C_1$–$C_4$ alkoxy) radical, a mesylamino($C_1$–$C_4$ alkoxy) radical or a carbamoylamino($C_1$–$C_4$ alkoxy) radical,
$R_4$ represents a hydrogen or halogen atom or a $C_1$–$C_4$ alkyl radical.

Among the nitrogen-containing groups of formula (I) above, there may be mentioned in particular the amino, mono($C_1$–$C_4$)alkylamino, ($C_1$–$C_4$)dialkylamino, ($C_1$–$C_4$) trialkylamino, monohydroxy($C_1$–$C_4$)alkylamino, imidazolinium and ammonium radicals.

Among the para-phenylenediamines of formula (I) above, there may be mentioned more particularly para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 2-methyl-1-N-β-hydroxyethyl-para-phenylenediamine and their addition salts with an acid.

Among the para-phenylenediamines of formula (I) above, there are most particularly preferred para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and their addition salts with an acid. (II) According to the invention, "double bases" is understood to mean the compounds containing at least two aromatic rings on which amino and/or hydroxyl groups are carried.

Among the double bases which can be used as oxidation bases in the dye compositions in accordance with the invention, there may be mentioned in particular the compounds corresponding to the following formula (II), and their addition salts with an acid:

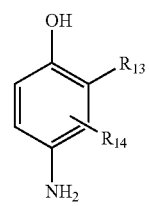

in which:

Z$_1$ and Z$_2$, which are identical or different, represent a hydroxyl or —NH$_2$ radical which may be substituted with a C$_1$–C$_4$ alkyl radical or with a linking arm Y;

the linking arm Y represents a linear or branched alkylene chain comprising from 1 to 14 carbon atoms, which may be interrupted by or which may end with one or more nitrogen-containing groups and/or one or more heteroatoms such as oxygen, sulfur or nitrogen atoms, and optionally substituted with one or more hydroxyl or C$_1$–C$_6$ alkoxy radicals;

R$_5$ and R$_6$ represent a hydrogen or halogen atom, a C$_1$–C$_4$ alkyl radical, a monohydroxy(C$_1$–C$_4$ alkyl) radical, a polyhydroxy(C$_2$–C$_4$ alkyl) radical, an amino(C$_1$–C$_4$ alkyl) radical or a linking arm Y;

R$_7$, R$_8$, R$_9$, R$_{10}$, R$_{11}$ and R$_{12}$, which are identical or different, represent a hydrogen atom, a linking arm Y or a C$_1$–C$_4$ alkyl radical;

it being understood that the compounds of formula (II) contain only one linking arm Y per molecule.

Among the nitrogen-containing groups of formula (II) above, there may be mentioned in particular the amino, mono(C$_1$–C$_4$)alkylamino, (C$_1$–C$_4$)dialkylamino, (C$_1$–C$_4$)trialkylamino, monohydroxy(C$_1$–C$_4$)alkylamino, imidazolinium and ammonium radicals.

Among the double bases of formulae (II) above, there may be mentioned more particularly N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and their addition salts with an acid.

Among these double bases of formula (II), N,N'-bis(β-hydroxyethyl)-N,N'-bis(4'-aminophenyl)-1,3-diaminopropanol, 1,8-bis(2,5-diaminophenoxy)-3,5-dioxaoctane or one of their addition salts with an acid are particularly preferred.

(III) the para-aminophenols corresponding to the following formula (III), and their addition salts with an acid:

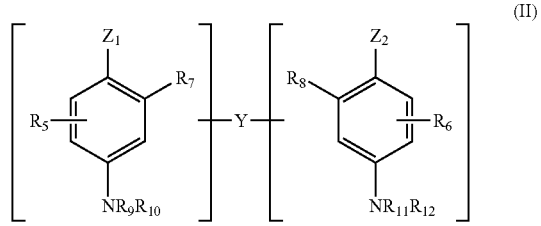

in which:

R$_{13}$ represents a hydrogen atom, a halogen atom such as fluorine, a C$_1$–C$_4$ alkyl, monohydroxy(C$_1$–C$_4$ alkyl), (C$_1$–C$_4$)alkoxy(C$_1$–C$_4$)alkyl or amino(C$_1$–C$_4$ alkyl) or hydroxy(C$_1$–C$_4$)alkylamino(C$_1$–C$_4$ alkyl) radical, R$_{14}$ represents a hydrogen atom or a halogen atom such as fluorine, a C$_1$–C$_4$ alkyl, monohydroxy(C$_1$–C$_4$ alkyl), polyhydroxy(C$_2$–C$_4$ alkyl), amino(C$_1$–C$_4$ alkyl), cyano (C$_1$–C$_4$ alkyl) or (C$_1$–C$_4$)alkoxy(C$_1$–C$_4$)alkyl radical.

Among the para-aminophenols of formula (III) above, there may be mentioned more particularly para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, and their addition salts with an acid.

(IV) the ortho-aminophenols which can be used as oxidation bases in the context of the present invention are in particular chosen from 2-aminophenol, 2-amino-1-hydroxy-5-methylbenzene, 2-amino-1-hydroxy-6-methylbenzene, 5-acetamido-2-aminophenol, and their addition salts with an acid.

(V) among the heterocyclic bases which can be used as oxidation bases in the dyeing compositions in accordance with the invention, there may be mentioned more particularly pyridine derivatives, pyrimidine derivatives, pyrazole derivatives, and their addition salts with an acid.

Among the pyridine derivatives, there may be mentioned more particularly the compounds described for example in Patents GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl) amino-3-amino-6-methoxypyridine, 3,4-diaminopyridine, and their addition salts with an acid.

Among the pyrimidine derivatives, there may be mentioned more particularly the compounds described for example in German Patent DE 2,359,399 or Japanese Patents JP 88-169,571 and JP 91-10659 or Patent Application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and the pyrazolopyrimidine derivatives such as those mentioned in Patent Application FR-A-2,750, 048 and among which there may be mentioned pyrazolo[1, 5-a]pyrimidine-3,7-diamine; 2,5-dimethylpyrazolo[1,5-a] pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo [1,5-a]pyrimidin-7-ylamino)ethanol; 2-(7-aminopyrazolo[1, 5-a]pyrimidin-3-ylamino)ethanol; 2-[(3-aminopyrazolo[1,5-a]pyrimidin-7-yl)(2-hydroxyethyl)amino]ethanol; 2-[(7-aminopyrazolo[1,5-a]pyrimidin-3-yl)(2-hydroxyethyl) amino]ethanol; 5,6-dimethylpyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine; 3-amino-5-methyl-7-imidazolylpropylaminopyrazolo[1,5-a]pyrimidine; and their addition salts and their tautomeric forms, when a tautomeric equilibrium exists, and their addition salts with an acid.

Among the pyrazole derivatives, there may be mentioned more particularly the compounds described in Patents DE 3,843,892, DE 4,133,957 and Patent Applications WO 94/08969, WO 94/08970, FR-A-2,733,749 and DE 195 43 988 such as 4,5-diamino-1-methylpyrazole, 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-β-hydroxyethyl)pyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl) amino-1-methylpyrazole, and their addition salts with an acid.

According to the present invention, the oxidation bases preferably represent from 0.0005 to 12% by weight approximately of the total weight of the composition and more preferably still from 0.005 to 8% by weight approximately of this weight.

The dye composition in accordance with the invention may contain one or more couplers chosen from those conventionally used in oxidation dyeing, and in particular from meta-aminophenols, meta-phenylenediamines, meta-diphenols, naphthols and heterocyclic couplers such as for example indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines and their addition salts with an acid.

These couplers are more particularly chosen from 2,4-diamino-1-(β-hydroxyethyloxy)benzene, 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, 2-amino-3-hydroxypyridine, 3,6-dimethylpyrazolo[3,2-c]-1,2,4-triazole, 2,6-dimethylpyrazolo[1,5-b]-1,2,4-triazole and their addition salts with an acid.

Generally, the coupler(s) preferably represent from 0.0001 to 15% by weight approximately of the total weight of the dye composition and still more preferably from 0.001 to 10% approximately.

The addition salts with an acid of these oxidation dyes (bases and/or couplers) are in particular chosen from hydrochlorides, hydrobromides, sulfates and tartrates, lactates and acetates.

The dye composition in accordance with the invention may additionally comprise one or more direct dyes in particular in order to modify the shades by increasing their glint. These direct dyes may be chosen in particular from neutral, cationic or anionic nitro, azo or anthraquinone dyes which are conventionally used or those which are described in particular in patent applications FR-2782450, 2782451, 2782452 and EP-1025834, in the proportion by weight of about 0.001 to 20% and preferably 0.01 to 10% of the total weight of the composition.

The appropriate dyeing medium for the composition is preferably an aqueous medium consisting of water and may advantageously contain cosmetically acceptable organic solvents which are different from (A) and (B) according to the present invention, including more particularly alcohols such as ethyl alcohol, isopropyl alcohol, benzyl alcohol and phenylethyl alcohol, glycol ethers such as, for example, monomethyl, monoethyl and monobutyl ethers of ethylene glycol, monomethyl ether of propylene glycol, alkyl ethers of diethylene glycol such as for example monoethyl ether or monobutyl ether of diethylene glycol. The solvents may then be present in concentrations of between about 0.5 and 20% and preferably between about 2 and 10% by weight relative to the total weight of the composition.

The dye composition according to the invention may additionally also comprise associative polymers.

Associative Polymers Used According to the Invention

Associative polymers are water-soluble polymers which are capable, in an aqueous medium, of reversibly combining with each other or with other molecules.

Their chemical structure comprises hydrophilic regions, and hydrophobic regions which are characterized by at least one fatty chain.

The associative polymers according to the invention may be of the anionic, cationic, amphoteric and preferably nonionic type.

Associative Polymers of the Anionic Type:

There may be mentioned among them:

(I) those comprising at least one hydrophilic unit and at least one allyl ether unit containing a fatty chain, more particularly those in which the hydrophilic unit consists of an ethylenic unsaturated anionic monomer, more particularly still of a vinylcarboxylic acid and most particularly of an acrylic acid, a methacrylic acid or mixtures thereof, and in which the allyl ether unit containing a fatty chain corresponds to the monomer having the following formula (I):

$$CH_2=CR'CH_2OB_nR \qquad (I)$$

in which R' denotes H or $CH_3$, B denotes the ethyleneoxy radical, n is zero or denotes an integer ranging from 1 to 100, R denotes a hydrocarbon radical chosen from the alkyl, arylalkyl, aryl, alkylaryl or cycloalkyl radicals, comprising from 8 to 30 carbon atoms, preferably 10 to 24, and more particularly still from 12 to 18 carbon atoms. A more particularly preferred unit of formula (I) is a unit in which R' denotes H, n is equal to 10, and R denotes a stearyl ($C_{18}$) radical.

Anionic associative polymers of this type are described and prepared, according to a method of polymerization in emulsion, in patent EP-0,216,479.

Among these anionic associative polymers, the polymers formed from 20 to 60% by weight of acrylic acid and/or of methacrylic acid, from 5 to 60% by weight of lower alkyl (meth)acrylates, from 2 to 50% by weight of allyl ether containing a fatty chain of formula (I), and from 0 to 1% by weight of a crosslinking agent which is a well-known copolymerizable polyethylenic unsaturated monomer such as diallyl phthalate, allyl (meth)acrylate, divinylbenzene, (poly)ethylene glycol dimethacrylate and methylenebisacrylamide, are particularly preferred according to the invention.

Among the latter, the crosslinked terpolymers of methacrylic acid, ethyl acrylate, polyethylene glycol (10 EO) stearyl alcohol ether (Steareth 10), in particular those sold by the company ALLIED COLLOIDS under the names SALCARE SC 80® and SALCARE SC 90® which are aqueous emulsions containing 30% of a crosslinked terpolymer of methacrylic acid, of ethyl acrylate and of steareth-10-allyl ether (40/50/10) are most particularly preferred.

(II) those comprising at least one hydrophilic unit of the olefinic unsaturated carboxylic acid type and at least one hydrophobic unit of the ($C_{10}$–$C_{30}$)alkyl ester of unsaturated carboxylic acid type.

Preferably, these polymers are chosen from those whose hydrophilic unit of the olefinic unsaturated carboxylic acid type corresponds to the monomer having the following formula (II):

(II)

in which $R_1$ denotes H or $CH_3$ or $C_2H_5$, that is to say acrylic acid, methacrylic acid or ethacrylic acid units, and whose hydrophobic unit of the ($C_{10}$–$C_{30}$)alkyl ester of unsaturated carboxylic acid type corresponds to the monomer having the following formula (III):

(III)

in which $R_2$ denotes H or $CH_3$ or $C_2H_5$ (that is to say acrylate, methacrylate or ethacrylate units) and preferably H (acrylate units) or $CH_3$ (methacrylate units), $R_3$ denoting a $C_{10}$–$C_{30}$, and preferably $C_{12}$–$C_{22}$, alkyl radical.

($C_{10}$–$C_{30}$)alkyl esters of unsaturated carboxylic acids in accordance with the invention comprise for example lauryl acrylate, stearyl acrylate, decyl acrylate, isodecyl acrylate, dodecyl acrylate, and the corresponding methacrylates, lauryl methacrylate, stearyl methacrylate, decyl methacrylate, isodecyl methacrylate and dodecyl methacrylate.

Anionic polymers of this type are for example described and prepared according to U.S. Pat. Nos. 3,915,921 and 4,509,949.

Among this type of anionic associative polymers, there will be more particularly used polymers formed from a mixture of monomers comprising:
(i) essentially acrylic acid,
(ii) an ester having the formula (III) described above and in which $R_2$ denotes H or $CH_3$, $R_3$ denoting an alkyl radical having from 12 to 22 carbon atoms,
(iii) and a crosslinking agent, which is a well-known copolymerizable polyethylenic unsaturated monomer such as diallyl phthalate, allyl (meth)acrylate, divinylbenzene, (poly)ethylene glycol dimethacrylate and methylenebisacrylamide.

Among this type of anionic associative polymers, there will be more particularly used those consisting of 95 to 60% by weight of acrylic acid (hydrophilic unit), 4 to 40% by weight of $C_{10}$–$C_{30}$ alkyl acrylate (hydrophobic unit), and 0 to 6% by weight of crosslinking polymerizable monomer, or alternatively those consisting of 98 to 96% by weight of acrylic acid (hydrophilic unit), 1 to 4% by weight of $C_{10}$–$C_{30}$ alkyl acrylate (hydrophobic unit) and 0.1 to 0.6% by weight of crosslinking polymerizable monomer such as those described above.

Among said above polymers, the products sold by the company GOODRICH under the trade names PEMULEN TR1®, PEMULEN TR2®, CARBOPOL 1382®, and still more preferably PEMULEN TR1®, and the product sold by the company S.E.P.P.I.C. under the name COATEX SX®, are most particularly preferred according to the present invention.

(III) the terpolymers of maleic anhydride/$C_{30}$–$C_{38}$ α-olefin/alkyl maleate such as the product (maleic anhydride/$C_{30}$–$C_{38}$ α-olefin/isopropyl maleate copolymer) sold under the name PERFORMA V 1608® by the company NEWPHASE TECHNOLOGIES.

(IV) the acrylic terpolymers comprising:
(a) about 20% to 70% by weight of a carboxylic acid with α,β-monoethylenic unsaturation,
(b) about 20 to 80% by weight of a nonsurfactant monomer with α,β-monoethylenic unsaturation different from (a),
(c) about 0.5 to 60% by weight of a nonionic monourethane which is the product of the reaction of a monohydric surfactant with a monoisocyanate with monoethylenic unsaturation, such as those described in patent application EP-A-0,173,109 and more particularly that described in Example 3, namely a methacrylic acid/methyl acrylate/dimethyl metaisopropenyl benzyl isocyanate of ethoxylated (40 EO) behenyl alcohol terpolymer in 25% aqueous dispersion.

(V) the copolymers comprising among their monomers a carboxylic acid with α,β-monoethylenic unsaturation and an ester of a carboxylic acid with α,β-monoethylenic unsaturation and an oxyalkylenated fatty alcohol.

Preferably, these compounds also comprise, as monomer, an ester of a carboxylic acid with α,β-monoethylenic unsaturation and a C1C4 alcohol.

By way of example of this type of compound, there may be mentioned ACULYN 22® sold by the company ROHM and HAAS, which is an oxyalkylenated stearyl methacrylate/ethyl acrylate/methacrylic acid terpolymer.

Associative Polymers of the Cationic Type

According to the present invention, they are preferably chosen from the quaternized cellulose derivatives and the polyacrylates with noncyclic amine-containing side groups.

The quaternized cellulose derivatives are in particular,
the quaternized celluloses modified by groups comprising at least one fatty chain, such as the alkyl, arylalkyl or alkylaryl groups comprising at least 8 carbon atoms, or mixtures thereof,
the quaternized hydroxyethylcelluloses modified by groups comprising at least one fatty chain, such as the alkyl, arylalkyl or alkylaryl groups comprising at least 8 carbon atoms, or mixtures thereof.

The alkyl radicals carried by the above quaternized celluloses or hydroxyethylcelluloses preferably comprise from 8 to 30 carbon atoms. The aryl radicals preferably denote phenyl, benzyl, naphthyl or anthryl groups.

There may be mentioned as examples of quaternized alkylhydroxyethylcelluloses containing $C_8$–$C_{30}$ fatty chains the products QUATRISOFT LM 200®, QUATRISOFT LM-X 529-18-A®, QUATRISOFT LM-X 529-18B® ($C_{12}$ alkyl) and QUATRISOFT LM-X 529-8® ($C_{18}$ alkyl) marketed by the company AMERCHOL and the products CRODACEL QM®, CRODACEL QL® ($C_{1-2}$ alkyl) and CRODACEL QS® ($C_{18}$ alkyl) marketed by the company CRODA.

Amphoteric Associative Polymers

They are preferably chosen from those containing at least one noncyclic cationic unit. Still more particularly, the ones that are preferred are those prepared from or comprising 1 to 20 mol % of monomer containing a fatty chain, and preferably 1.5 to 15 mol % and still more particularly 1.5 to 6 mol %, relative to the total number of moles of monomers.

The preferred amphoteric associative polymers according to the invention comprise, or are prepared by copolymerizing:

1) at least one monomer of formula (Ia) or (Ib):

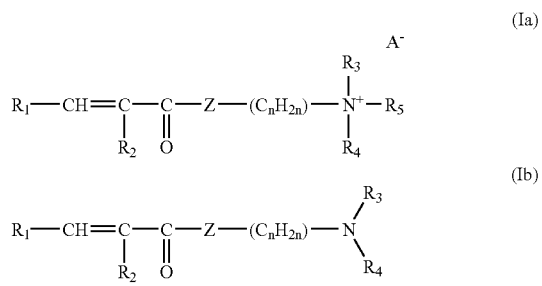

in which $R_1$ and $R_2$, which are identical or different, represent a hydrogen atom or a methyl radical, $R_3$, $R_4$ and $R_5$, which are identical or different, represent a linear or branched alkyl radical having from 1 to 30 carbon atoms,
Z represents an NH group or an oxygen atom,
n is an integer from 2 to 5,
$A^-$ is an anion derived from an organic or inorganic acid, such as a methosulfate anion or a halide such as chloride or bromide;

2) at least one monomer of formula (II)

$$R_6\text{—}CH\text{=}CR_7\text{—}COOH \qquad (II)$$

in which $R_6$ and $R_7$, which are identical or different, represent a hydrogen atom or a methyl radical;

and 3) at least one monomer of formula (III):

$$R_6\text{—}CH\text{=}CR_7\text{—}COXR_8 \qquad (III)$$

in which $R_6$ and $R_7$, which are identical or different, represent a hydrogen atom or a methyl radical, X denotes an oxygen or nitrogen atom and $R_8$ denotes a linear or branched alkyl radical having from 1 to 30 carbon atoms;
at least one of the monomers of formula (Ia), (Ib) or (III) containing at least one fatty chain.

The monomers of formula (Ia) and (Ib) of the present invention are preferably chosen from the group consisting of:
dimethylaminoethyl methacrylate, dimethylaminoethyl acrylate,
diethylaminoethyl methacrylate, diethylaminoethyl acrylate,
dimethylaminopropyl methacrylate, dimethylaminopropyl acrylate,
dimethylaminopropylmethacrylamide, dimethylaminopropylacrylamide, these monomers being optionally quaternized, for example with a $C_1$–$C_4$ alkyl halide or a $C_1$–$C_4$ dialkyl sulfate.

More particularly, the monomer of formula (Ia) is chosen from acrylamidopropyltrimethylammonium chloride and methacrylamidopropyltrimethylammonium chloride.

The monomers of formula (II) of the present invention are preferably chosen from the group consisting of acrylic acid, methacrylic acid, crotonic acid and 2-methylcrotonic acid. More particularly, the monomer of formula (II) is acrylic acid.

The monomers of formula (III) of the present invention are preferably chosen from the group consisting of $C_{12}$–$C_{22}$, and more particularly $C_{16}$–$C_{18}$ alkyl acrylates or methacrylates.

The monomers constituting the amphoteric polymers containing a fatty chain of the invention are preferably already neutralized and/or quaternized.

The ratio of the number of cationic charges/anionic charges is preferably equal to about 1.

The amphoteric associative polymers according to the invention preferably comprise from 1 to 10 mol % of the monomer containing a fatty chain (monomer of formula (Ia), (Ib) or (III)), and preferably from 1.5 to 6 mol %.

The weight-average molecular weights of the amphoteric associative polymers according to the invention may vary from 500 to 50 000 000 and are preferably between 10 000 and 5 000 000.

The amphoteric associative polymers according to the invention may also contain other monomers such as nonionic monomers and in particular such as $C_1$–$C_4$ alkyl acrylates or methacrylates.

Amphoteric associative polymers according to the invention are for example described and prepared in Patent Application WO9844012.

Among the amphoteric associative polymers according to the invention, the acrylic acid/(meth)acrylamidopropyltrimethylammonium chloride/stearyl methacrylate terpolymers are preferred.

Preferred dyeing compositions according to the invention comprise an associative polymer of the nonionic type.

Associative Polymers of the Nonionic Type

According to the invention, they are preferably chosen from:

(1) celluloses modified by groups comprising at least one fatty chain; there may be mentioned by way of example:
   the hydroxyethylcelluloses modified by groups comprising at least one fatty chain such as alkyl, arylalkyl or alkylaryl groups, or mixtures thereof, and in which the alkyl groups are preferably $C_8$–$C_{22}$, such as the product NATROSOL PLUS GRADE 330 CS® ($C_{16}$ alkyls) sold by the company AQUALON, or the product BERMOCOLL EHM 100® sold by the company BEROL NOBEL,
   those modified by polyalkylene glycol ether of alkylphenol groups, such as the product AMERCELL POLYMER HM-1500® (polyethylene glycol (15) ether of nonylphenol) sold by the company AMERCHOL.

(2) hydroxypropylguars modified by groups comprising at least one fatty chain such as the product ESAFLOR HM 22® ($C_{22}$ alkyl chain) sold by the company LAMBERTI, the products RE210-18® ($C_{14}$ alkyl chain) and RE205-1® ($C_{20}$ alkyl chain) sold by the company RHONE POULENC.

(3) copolymers of vinylpyrrolidone and of hydrophobic monomers having a fatty chain, of which there may be mentioned by way of example:
   the products ANTARON V216® or GANEX V216® (vinylpyrrolidone/hexadecene copolymer) sold by the company I.S.P.
   the products ANTARON V220® or GANEX V220® (vinylpyrrolidone/eicosene copolymer) sold by the company I.S.P.

(4) copolymers of $C_1$–$C_6$ alkyl methacrylates or acrylates and of amphiphilic monomers comprising at least one fatty chain such as for example the oxyethylenated stearyl acrylate/methyl acrylate copolymer sold by the company GOLDSCHMIDT under the name ANTIL 208®.

(5) copolymers of hydrophilic methacrylates or acrylates and of hydrophobic monomers comprising at least one fatty chain such as for example the polyethylene glycol methacrylate/lauryl methacrylate copolymer.

(6) polyether-polyurethanes comprising in their chain both hydrophilic sequences which are most often of a polyoxyethylenated nature and hydrophobic sequences which may be aliphatic chains alone and/or cycloaliphatic and/or aromatic chains.

(7) polymers containing an aminoplast ether backbone possessing at least one fatty chain, such as the compounds PURE THIX® provided by the company SUD-CHEMIE.

Preferably, the polyether-polyurethanes comprise at least two lipophilic hydrocarbon chains, having from 6 to 30 carbon atoms, separated by a hydrophilic sequence, it being possible for the hydrocarbon chains to be pendent chains or chains at the end of a hydrophilic sequence. In particular, it is possible for one or more pendent chains to be envisaged. In addition, the polymer may comprise a hydrocarbon chain at one end or at both ends of a hydrophilic sequence.

The polyether-polyurethanes may be polyblocks, in particular in triblock form. The hydrophobic sequences may be at each end of the chain (for example: triblock copolymer with hydrophilic central sequence) or distributed both at the ends and in the chain (polyblock copolymer for example). These same polymers may also be in the form of graft units or may be star-shaped.

The nonionic polyether-polyurethanes containing a fatty chain may be triblock copolymers whose hydrophilic sequence is a polyoxyethylenated chain comprising from 50 to 1000 oxyethylenated groups. Nonionic polyether-polyurethanes comprise a urethane bond between the hydrophilic sequences, hence the origin of the name.

By extension, those whose hydrophilic sequences are linked by other chemical bonds to the lipophilic sequences are also included among the nonionic polyether-polyurethanes containing a fatty chain.

By way of examples of nonionic polyether-polyurethanes containing a fatty chain which can be used in the invention, it is also possible to use Rheolate® 205 containing a urea functional group sold by the company RHEOX or the Rheolates® 208, 204 or 212, as well as Acrysol RM 184®.

There may also be mentioned the product ELFACOS T210® containing a $C_{12-14}$ alkyl chain and the product ELFACOS T212® containing a $C_{18}$ alkyl chain from AKZO.

The product DW 1206B® from RHOM & HAAS containing a $C_{20}$ alkyl chain and with a urethane bond, provided at 20% dry matter content in water, may also be used.

It is also possible to use solutions or dispersions of these polymers in particular in water or in an aqueous-alcoholic medium. By way of example of such polymers, there may be mentioned Rhéolate® 255, Rhéolate® 278 and Rhéolate® 244 sold by the company RHEOX. It is also possible to use the product DW 1206F and DW 1206J provided by the company ROHM & HAAS.

The polyether-polyurethanes which can be used according to the invention are in particular those described in the article by G. Formum, J. Bakke and Fk. Hansen-Colloid Polym. Sci 271, 380–389 (1993).

Still more particularly, according to the invention, it is preferable to use a polyether-polyurethane which can be obtained by polycondensation of at least three compounds comprising (i) at least one polyethylene glycol comprising from 150 to 180 mol of ethylene oxide, (ii) stearyl alcohol or decyl alcohol and (iii) at least one diisocyanate.

Such polyether-polyurethanes are sold in particular by the company ROHM & HMS under the names Aculyn 46® and Aculyn 44®D [ACULYN 46® is a polycondensate of polyethylene glycol containing 150 or 180 mol of ethylene oxide, stearyl alcohol and methylenebis(4-cyclohexyl isocyanate) (SMDI), at 15% by weight in a matrix of maltodextrin (4%) and water (81%); ACULYN 44® is a polycondensate of polyethylene glycol containing 150 or 180 mol of ethylene oxide, decyl alcohol and methylenebis(4-cyclohexyl isocyanate) (SMDI), at 35% by weight in a mixture of propylene glycol (39%) and water (26%)].

The associative polymers of the nonionic, anionic, cationic or amphoteric type are preferably used in a quantity which may vary from about 0.1 to 10% by weight of the total weight of the dyeing composition. More preferably, this quantity varies from about 0.5 to 5% by weight, and still more particularly from about 1 to 3% by weight.

The dye composition according to the invention may also contain surfactants different from the oxyalkylenated or polyglycerolated $C_{12}$–$C_{30}$ fatty alcohols according to the invention and chosen from those of the anionic, nonionic, cationic, amphoteric or zwitterionic type, in the proportion of at least 0.01% by weight relative to the total weight of the composition.

These surfactants may be chosen from:

Nonionic Surfactants:

The nonionic surfactants themselves are also compounds which are well known per se (in this respect see especially the "Handbook of Surfactants" by M. R. Porter, published by Blackie & Son (Glasgow and London), 1991, pp. 116–178) and, in the context of the present invention, their nature does not assume any critical character. They can thus be chosen especially from (nonlimiting list) alpha-diols or polyethoxylated or polypropoxylated alkylphenols which have a fatty chain containing, for example, 8 to 18 carbon atoms, it being possible for the number of ethylene oxide or propylene oxide groups to range especially from 2 to 50. The copolymers of ethylene oxide and propylene oxide and the condensates of ethylene oxide and propylene oxide with fatty alcohols may also be mentioned; the polyethoxylated fatty amides preferably containing from 2 to 30 mol of ethylene oxide, the polyglycerolated fatty amides containing on average 1 to 5 glycerol groups and in particular 1.5 to 4; the polyethoxylated fatty amines preferably containing 2 to 30 mol of ethylene oxide; the oxyethylenated fatty acid esters of sorbitan containing from 2 to 30 mol of ethylene oxide; the fatty acid esters of sucrose, the fatty acid esters of polyethylene glycol, alkylpolyglycosides, the N-alkylglucamine derivatives, amine oxides such as the oxides of $(C_{10}$–$C_{14})$-alkylamines or the N-acylaminopropylmorpholine oxides.

Anionic Surfactants:

By way of example of anionic surfactants which can be used, alone or as mixtures, in the context of the present invention there may be mentioned in particular (nonlimiting list) the salts (in particular alkali metal, especially sodium, salts, ammonium salts, amine salts, amino alcohol salts or magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamidesulfonates, alkylaryl sulfonates, α-olefinsulfonates, paraffinsulfonates; $(C_6$–$C_{24})$ alkyl sulfosuccinates, $(C_6$–$C_{24})$alkyl ether sulfosuccinates, $(C_6$–$C_{24})$alkylamide sulfosuccinates; $(C_6$–$C_{24})$alkyl sulfoacetates; $(C_6$–$C_{24})$acyl sarcosinates and $(C_6$–$C_{24})$acyl glutamates. It is also possible to use $(C_6$–$C_{24})$alkyl polyglycoside carboxylic esters such as alkyl glucoside citrates, alkyl polyglycoside tartrate and alkyl polyglycoside sulfosuccinates, alkyl sulfosuccinamates; acyl isethionates and N-acyltaurates, the alkyl or acyl radical of all these various compounds preferably comprising from 12 to 20 carbon atoms, and the aryl radical preferably denoting a phenyl or benzyl group. Among the anionic surfactants which can still be used, there may also be mentioned the acyllactylates whose acyl radical comprises 8 to 20 carbon atoms. It is also possible to use the alkyl D-galactosideuronic acids and their salts, the polyoxyalkylenated $(C_6$–$C_{24})$alkyl ether carboxylic acids, the polyoxyalkylenated $(C_6$–$C_{24})$alkyl ether carboxylic acids, the polyoxyalkylenated $(C_6$–$C_{24})$alkyl amidoether carboxylic acids and salts thereof, in particular those comprising from 2 to 50 alkylene, in particular ethylene, oxide groups, and mixtures thereof.

Amphoteric or Zwitterionic Surfactants:

The amphoteric or zwitterionic surfactants, the nature of which is not of critical importance in the context of the present invention, may be especially (nonlimiting list) derivatives of aliphatic secondary or tertiary amines in which the aliphatic radical is a linear or branched chain containing 8 to 18 carbon atoms and containing at least one water-solubilizing anionic group (for example carboxylate, sulfonate, sulfate, phosphate or phosphonate); $(C_8$–$C_{20})$ alkylbetaines, sulfobetaines, $(C_8$–$C_{20})$alkylamido$(C_1$–$C_6)$ alkylbetaines or $(C_8$–$C_{20})$alkylamido$(C_1$–$C_6)$alkylsulfobetaines may further be mentioned.

Among the amine derivatives, there may be mentioned the products sold under the name MIRANOL, as described in U.S. Pat. No. 2,528,378 and U.S. Pat. No. 2,781,354 and classified in the CTFA dictionary, 3rd edition, 1982, under the names Amphocarboxyglycinates and Amphocarboxypropionates having the respective structures:

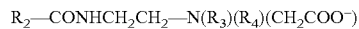

$R_2$—CONHCH$_2$CH$_2$—N(R$_3$)(R$_4$)(CH$_2$COO$^-$)

in which: $R_2$ denotes an alkyl radical of an acid $R_2$—COOH present in hydrolyzed copra oil, a heptyl, nonyl or undecyl radical, $R_3$ denotes a beta-hydroxyethyl group and $R_4$ a carboxymethyl group;

and

$R_2'$—CONHCH$_2$CH$_2$—N(B)(C)

in which:

B represents —CH$_2$CH$_2$OX', C represents —(CH$_2)_z$—Y', with z=1 or 2,

X' denotes the —CH$_2$CH$_2$—COOH group or a hydrogen atom

Y' denotes —COOH or the radical —CH$_2$—CHOH—SO$_3$H $R_2'$ denotes an alkyl radical of an acid $R_9$—COOH present in copra oil or in hydrolyzed linseed oil, an alkyl radical, especially $C_7$, $C_9$, $C_{11}$ or $C_{13}$, a $C_{17}$ alkyl radical and its iso form or an unsaturated $C_{17}$ radical.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Capryloamphodipropionate, Lauro-amphodipropionic acid, Cocoamphodipropionic acid.

By way of example, there may be mentioned the cocoamphodiacetate marketed under the trade name MIRANOL® C2M concentrate by the company RHODIA CHIMIE.

Cationic Surfactants:

Among the cationic surfactants, there may be mentioned in particular (nonlimiting list): the salts of optionally polyoxyalkylenated primary, secondary or tertiary fatty amines; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives or amine oxides of a cationic nature.

The dye composition according to the invention may additionally contain at least one cationic or amphoteric polymer (different from the associative polymers according to the invention) in the proportion of at least 0.01% by weight relative to the total weight of the composition.

Cationic Polymers

For the purposes of the present invention, the expression "cationic polymer" denotes any polymer containing cationic groups and/or groups which can be ionized to cationic groups.

The cationic polymers which can be used in accordance with the present invention may be chosen from all those already known per se to improve the cosmetic properties of hair, namely in particular those described in Patent Application EP-A-337 354 and in French patents FR-2,270,846, 2,383,660, 2,598,611, 2,470,596 and 2,519,863.

The preferred cationic polymers are chosen from those which contain units comprising primary, secondary, tertiary and/or quaternary amine groups which may either form part of the principal polymeric chain, or be carried by a side substituent directly linked thereto.

The cationic polymers used generally have a number-average molecular mass of between 500 and $5 \times 10^6$ approximately, and preferably between $10^3 \times 3.10^6$ approximately.

Among the cationic polymers, there may be mentioned more particularly the polymers of the polyamine, polyamino amide and quaternary polyammonium type.

These are known products. They are described in particular in French patents No. 2,505,348 or 2,542,997. Among said polymers, there may be mentioned:

(1) The homopolymers or copolymers derived from acrylic or methacrylic esters or amides and comprising at least one of the units of the following formulae (I), (II), (III) or (IV):

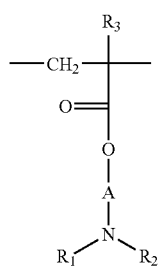

(I)

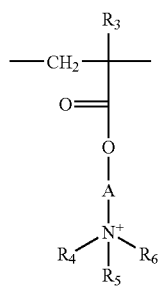

(II)

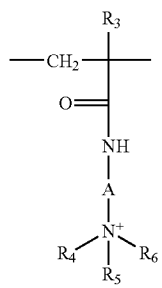

(III)

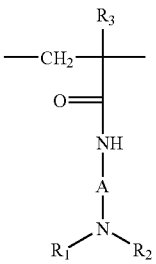

(IV)

in which:

$R_3$, which are identical or different, denote a hydrogen atom or a $CH_3$ radical;

A, which are identical or different, represent a linear or branched alkyl group of 1 to 6 carbon atoms, preferably 2 or 3 carbon atoms, or a hydroxyalkyl group of 1 to 4 carbon atoms;

$R_4$, $R_5$, $R_6$, which are identical or different, represent an alkyl group having from 1 to 18 carbon atoms or a benzyl radical and preferably an alkyl group having from 1 to 6 carbon atoms;

$R_1$ and $R_2$, which are identical or different, represent hydrogen or an alkyl group having from 1 to 6 carbon atoms and preferably methyl or ethyl;

X denotes an anion derived from an inorganic or organic acid such as a methosulfate anion or a halide such as chloride or bromide.

The polymers of the family (1) may contain, in addition, one or more units derived from comonomers which may be chosen from the family of acrylamides, methacrylamides, diacetone acrylamides, acrylamides and methacrylamides substituted on the nitrogen with lower ($C_1$–$C_4$)alkyls, acrylic or methacrylic acids or esters thereof, vinyllactams such as vinylpyrrolidone or vinylcaprolactam, vinyl esters.

Thus, among these polymers of the family (1), there may be mentioned:

the copolymers of acrylamide and dimethylamino-ethyl methacrylate quaternized with dimethyl sulfate or with a dimethyl halide such as that sold under the name HERCOFLOC® by the company HERCULES, the copolymers of acrylamide and methacryloyloxy-ethyltrimethylammonium chloride described, for example, in Patent Application EP-A-080976 and sold under the name BINA QUAT P 100® by the company CIBA GEIGY, the copolymer of acrylamide and methacryloyloxy-ethyltrimethylammonium methosulfate sold under the name RETEN® by the company HERCULES, the vinylpyrrolidone/dialkylaminoalkyl acrylate or methacrylate copolymers, quaternized or otherwise, such as the products sold under the name "GAFQUAT®" by the company ISP such as for example "GAFQUAT 734" or "GAFQUAT 755" or alternatively the products called "COPOLYMER 845®, 958® and 937®". These polymers are described in detail in French Patents 2,077,143 and 2,393,573, the dimethylaminoethyl methacrylate/vinylcapro-lactam/vinylpyrrolidone terpolymers such as the product sold under the name GAFFIX VC 713® by the company ISP, the vinylpyrrolidone/methacrylamidopropyldimethyl-amine copolymers marketed in particular under the name STYLEZE CC 10® by ISP, and the quaternized vinylpyrrolidone/dimethyl-aminopropyl methacrylamide copolymers such as the product sold under the name "GAFQUAT HS 100®" by the company ISP.

(2) The cellulose ether derivatives comprising quaternary ammonium groups, described in French Patent 1,492,597, and in particular the polymers marketed under the names "JR®" (JR 400, JR 125, JR 30M) or "LR®" (LR 400, LR 30M) by the company Union Carbide Corporation. These polymers are also defined in the CTFA dictionary as hydroxyethyl cellulose quaternary ammoniums which have reacted with an epoxide substituted by a trimethylammonium group.

(3) Cationic cellulose derivatives such as cellulose copolymers or cellulose derivatives grafted with a quaternary ammonium water-soluble monomer, and described especially in U.S. Pat. No. 4,131,576, such as hydroxyalkyl celluloses like hydroxymethyl, hydroxyethyl or hydroxypropyl celluloses grafted especially with a methacryloylethyltrimethylammonium, methacrylamidopropyltrimethylammonium or dimethyldiallylammonium salt.

The commercial products corresponding to this definition are more particularly the products sold under the name "Celquat L 200®" and "Celquat H 100®" by the company National Starch.

(4) The cationic polysaccharides described more particularly in U.S. Pat. Nos. 3,589,578 and 4,031,307 such as guar gums containing cationic trialkylammonium groups. Guar gums modified with a 2,3-epoxypropyltri-methylammonium salt (e.g. chloride) are for example used.

Such products are marketed in particular under the trade names JAGUAR C13 S®, JAGUAR C 15®, JAGUAR C 17@ or JAGUAR C162® by the company MEYHALL.

(5) Polymers consisting of piperazinyl units and of alkylene or hydroxyalkylene divalent radicals with straight or branched chains, optionally interrupted by oxygen, sulfur or nitrogen atoms or by aromatic or heterocyclic rings, as well as the oxidation and/or quaternization products of these polymers. Such polymers are described especially in French patents 2,162,025 and 2,280,361.

(6) Water-soluble polyaminoamides prepared in particular by polycondensation of an acid compound with a polyamine; these polyaminoamides may be crosslinked with an epihalohydrin, a diepoxide, a dianhydride, an unsaturated dianhydride, a diunsaturated derivative, a bishalohydrin, a bisazetidinium, a bishaloacyldiamine, an alkylbishalide or else with an oligomer resulting from the reaction of a difunctional compound which is reactive toward a bishalohydrin, a bisazetidinium, a bishaloacyldiamine, an alkylbishalide, an epihalohydrin, a diepoxide or a diunsaturated derivative; the crosslinking agent being employed in proportions ranging from 0.025 to 0.35 mol per amine group of the polyaminoamide; these polyaminoamides may be alkylated or, if they include one or more tertiary amine functional groups, quaternized. Such polymers are described especially in French Patents 2,252,840 and 2,368,508.

(7) Polyaminoamide derivatives resulting from the condensation of polyalkylenepolyamines with polycarboxylic acids, followed by an alkylation with difunctional agents. There may be mentioned, for example, the adipic acid/dialkylaminohydroxyalkyldialkylenetriamine polymers in which the alkyl radical contains from 1 to 4 carbon atoms and preferably denotes methyl, ethyl or propyl. Such polymers are described especially in French Patent 1,583,363.

Among these derivatives there may be mentioned more particularly the adipic acid/dimethyl-aminohydroxypropyl/diethylenetriamine polymers sold under the name "Cartaretine® F, F4 or F8" by the company Sandoz.

(8) Polymers obtained by reaction of a polyalkylenepolyamine containing two primary amine groups and at least one secondary amine group with a dicarboxylic acid chosen from diglycolic acid and saturated aliphatic dicarboxylic acids containing from 3 to 8 carbon atoms. The molar ratio of the polyalkylenepolyamine to the dicarboxylic acid being between 0.8:1 and 1.4:1; the polyaminoamide resulting therefrom being made to react with epichlorohydrin in a molar ratio of epichlorohydrin relative to the secondary amine group of the polyaminoamide of between 0.5:1 and 1.8:1. Such polymers are described especially in U.S. Pat. Nos. 3,227,615 and 2,961,347.

Polymers of this type are marketed in particular under the name "Hercosett 57®" by the company Hercules Inc. or else under the name of "PD 170®" or "Delsefte 101®" by the company Hercules in the case of the copolymer of adipic acid/epoxypropyl/diethylenetriamine.

(9) Cyclopolymers of dialkyldiallylammonium, such as the homopolymers or copolymers comprising, as main constituent of the chain, units corresponding to the formula (V):

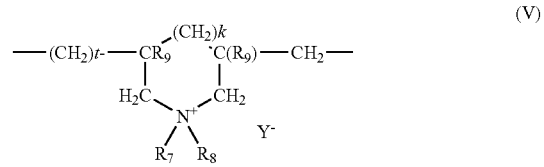

in which k and t are equal to 0 or 1, the sum k+t being equal to 1;

$R_7$ and $R_8$, which are identical or different, denote an alkyl group having from 1 to 8 carbon atoms, a $(C_1-C_5)$ hydroxyalkyl group, a $(C_1-C_4)$ amidoalkyl group, or $R_7$ and $R_8$ denote, together with the nitrogen atom to which they are attached, a piperidinyl or morpholinyl group;

$R_9$ denotes a hydrogen atom or a methyl radical;

$R_7$ and $R_8$, independently of each other, preferably denote an alkyl group having from 1 to 4 carbon atoms; $Y^-$ is an anion such as bromide, chloride, acetate, borate, citrate, tartrate, bisulfate, bisulfite, sulfate or phosphate. These polymers are described especially in French Patent 2,080,759 and in its certificate of addition 2,190,406.

Among the polymers defined above there may be mentioned more particularly the dimethyldiallylammonium chloride homopolymer sold under the name "Merquat 100®" by the company Calgon (and its homolog of low weight-average molecular mass) and the copolymers of diallyl-dimethylammonium chloride and acrylamide marketed under the name "MERQUAT 550®".

(10) The quaternary diammonium polymer containing repeating units corresponding to the formula:

in which formula (VII):

$R_{10}$, $R_{11}$, $R_{12}$ and $R_{13}$, which are identical or different, represent aliphatic, alicyclic or arylaliphatic radicals containing from 1 to 20 carbon atoms or lower aliphatic hydroxyalkyl radicals, or else $R_{10}$, $R_{11}$, $R_{12}$ and $R_{13}$, together or separately, form, with the nitrogen atoms to which they are attached, heterocycles optionally containing a second heteroatom other than nitrogen, or else $R_{10}$, $R_{11}$, $R_{12}$ and $R_{13}$ denote a linear or branched $C_1$–$C_6$ alkyl radical substituted by a nitrile, ester, acyl, amide or —CO—O—$R_{14}$—D or —CO—NH—$R_{14}$—D group where $R_{14}$ is an alkylene and D a quaternary ammonium group;

$A_1$ and $B_1$ represent polymethylene groups containing from 2 to 20 carbon atoms which may be linear or branched, saturated or unsaturated and which may contain, bonded to or inserted into the main chain, one or more aromatic rings, or one or more oxygen or sulfur atoms or sulfoxide, sulfone, disulfide, amino, alkylamino, hydroxyl, quaternary ammonium, ureido, amide or ester groups, and $X^-$ denotes an anion derived from an inorganic or organic acid;

$A_1$, $R_{10}$ and $R_{12}$, with the two nitrogen atoms to which they are attached, may form a piperazine ring; in addition, if $A_1$ denotes a saturated or unsaturated, linear or branched alkylene or hydroxyalkylene radical, $B_1$ may also denote a group —$(CH_2)_n$—CO—D—OC—$(CH_2)_n$— in which D denotes:

a) a glycol residue of formula: —O—Z—O—, where Z denotes a linear or branched hydrocarbon radical or a group corresponding to one of the following formulae:

—$(CH_2$—$CH_2$—$O)_x$—$CH_2$—$CH_2$—

—$[CH_2$—$CH(CH_3)$—$O]_y$—$CH_2$—$CH(CH_3)$— where x and y denote an integer from 1 to 4, representing a defined and unique degree of polymerization, or any number from 1 to 4, representing a mean degree of polymerization;

b) a bis-secondary diamine residue such as a piperazine derivative;

c) a bis-primary diamine residue of formula: —NH—Y—NH—, where Y denotes a linear or branched hydrocarbon radical or else the divalent radical

—$CH_2$—$CH_2$—S—S—$CH_2$—$CH_2$—;

d) a ureylene group of formula: —NH—CO—NH—.

$X^-$ is preferably an anion such as chloride or bromide.

These polymers have a number-average molecular mass which is generally between 1000 and 100 000.

Polymers of this type are described especially in French Patents 2,320,330, 2,270,846, 2,316,271, 2,336,434 and 2,413,907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is possible to use more particularly the polymers which consist of repeat units corresponding to the following formula (VIII):

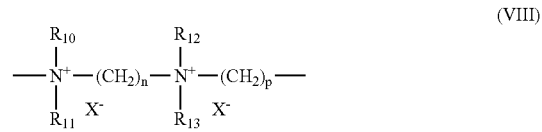

in which $R_{10}$, $R_{11}$, $R_{12}$ and $R_{13}$, which are identical or different, denote an alkyl or hydroxyalkyl radical having from 1 to 4 carbon atoms approximately, n and p are integers varying from 2 to 20 approximately and $X^-$ is an anion derived from an inorganic or organic acid.

(11) The quaternary polyammonium polymers consisting of repeating units of formula (IX):

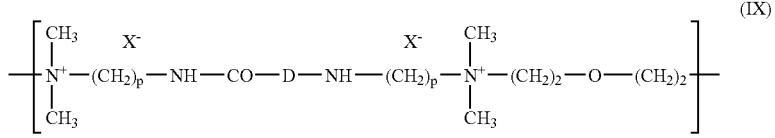

in which p denotes an integer varying from 1 to 6 approximately, D may be zero or may represent a group —$(CH_2)_r$—CO— in which r denotes a number equal to 4 or to 7, $X^-$ is an anion. Such polymers may be prepared according to the methods described in U.S. Pat. Nos. 4,157,388, 4,702,906, 4,719,282. They are in particular described in Patent Application EP-A-122 324.

Among these, there may be mentioned for example the products "Mirapol A 15®", "Mirapol AD1®", "Mirapol AZ1®" and "Mirapol 175®" sold by the company Miranol.

(12) Quaternary vinylpyrrolidone and vinylimidazole polymers such as, for example, the products marketed under the names Luviquat FC 905®, FC 550® and FC 370® by the company B.A.S.F.

(13) Polyamines like the Polyquart H® sold by Henkel, referenced under the name of "Polyethylene glycol (15) Tallow Polyamine" in the CTFA dictionary.

(14) The crosslinked polymers of methacryloyloxy($C_1$–$C_4$ alkyl)tri($C_1$–$C_4$ alkyl)ammonium salts such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. More particularly, it is possible to employ a crosslinked acrylamide/methacryloyloxyethyltrimethylammonium chloride copolymer (20/80 by weight) in the form of a dispersion containing 50% by weight of said copolymer in mineral oil. This dispersion is marketed under the name of "SALCARE® SC 92" by the company ALLIED COLLOIDS. It is also possible to employ a crosslinked methacryloyloxyethyltrimethylammonium chloride homopolymer containing approximately 50% by weight of the homopolymer in mineral oil or in a liquid ester. These dispersions are marketed under the names of "SALCARE® SC 95" and "SALCARE® SC 96" by the company ALLIED COLLOIDS.

Other cationic polymers that may be employed within the scope of the invention are polyalkyleneimines, in particular polyethyleneimines, polymers containing vinylpyridine or vinylpyridinium units, condensates of polyamines and of epichlorohydrin, quaternary polyureylenes and chitin derivatives.

Among all the cationic polymers which can be used in the context of the present invention, it is preferable to use the polymers of the families (9), (10) and (11) and still more preferably the following polymers:

1/the homopolymer of dimethyldiallylammonium chloride (family 9);

2/the polymers containing the repeating units of formula (VIII) described above (family 10) and for which $R_{10}$, $R_{11}$, $R_{12}$ and $R_{13}$ represent a methyl radical, n=3, p=6 and X=Cl, and in particular those whose molecular weight, determined by gel permeation chromatography, is between 9500 and 9900 [Polymer W having the formula below]; $R_{10}$ and $R_{11}$ represent a methyl radical, $R_{12}$ and $R_{13}$ represent an ethyl radical and n=p=3 and X=Br, and in particular those whose molecular weight, determined by gel permeation chromatography, is about 1200 [Polymer U having the formula below].

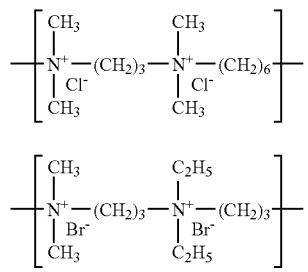

Said polymers with the units (W) and (U) are prepared and described in French Patent 2 270 846.

3/the polymers containing the units of formula (IX) described above (family 11), for which p is equal to 3, and, a) D denotes the value zero, X denotes a chlorine atom, the molecular mass measured by Carbon 13 NMR ($^{13}$C NMR) being about 25 500; a polymer of this type is sold by the company MIRANOL under the name MIRAPOL-A15®, b) D represents a group —$(CH_2)_4$—CO—, X denotes a chlorine atom, the molecular mass measured by Carbon 13 NMR ($^{13}$C NMR) being about 5600; a polymer of this type is provided by the company MIRANOL under the name of MIRAPOL-AD1®, c) D represents a group —$(CH_2)_7$—CO—, X denotes a chlorine atom, the molecular mass measured by Carbon 13 NMR ($^{13}$C NMR) being about 8100; a polymer of this type is provided by the company MIRANOL under the name MIRAPOL-AZ1®, d) a "Block Copolymer" consisting of units corresponding to the polymers described in paragraphs a) and b), provided by the company MIRANOL under the names MIRAPOL-9®, (molecular mass $^{13}$C NMR, about 7800), MIRAPOL-175®, (molecular mass $^{13}$C NMR, about 8000), MIRAPOL-95®, (molecular mass $^{13}$C NMR, about 12 500). Still more particularly, the polymer containing the units of formula (IX) are preferred according to the invention in which p is equal to 3, D denotes the value zero, X denotes a chlorine atom, the molecular mass measured by Carbon 13 NMR ($^{13}$C NMR) being about 25 500 (Mirapol-A15®).

Amphoteric Polymers

The amphoteric polymers which can be used in accordance with the present invention may be chosen from the polymers containing K and M units distributed statistically in the polymer chain where K denotes a unit which is derived from a monomer containing at least one basic nitrogen atom and M denotes a unit which is derived from an acidic monomer containing one or more carboxylic or sulfonic groups or alternatively K and M may denote groups which are derived from zwitterionic monomers of carboxybetaines or of sulfobetaines;

K and M may also denote a cationic polymer chain containing primary, secondary, tertiary or quaternary amine groups, in which at least one of the amine groups carries a carboxylic or sulfonic group linked via a hydrocarbon radical or alternatively K and M form part of a chain of a polymer with an α,β-dicarboxylic ethylene unit in which one of the carboxylic groups has been caused to react with a polyamine containing one or more primary or secondary amine groups.

The amphoteric polymers corresponding to the definition given above which are more particularly preferred are chosen from the following polymers:

(1) The polymers resulting from the copolymerization of a monomer derived from a vinyl compound carrying a carboxylic group such as more particularly acrylic acid, methacrylic acid, maleic acid, alpha-chloroacrylic acid, and of a basic monomer derived from a substituted vinyl compound containing at least one basic atom such as more particularly dialkylaminoalkyl methacrylate and acrylate, dialkylaminoalkylmethacrylamide and acrylamide. Such compounds are described in U.S. Pat. No. 3,836,537. Mention may also be made of the sodium acrylate/acrylamidopropyltrimethylammonium chloride copolymer sold under the name POLYQUART KE 3033® by the company HENKEL.

The vinyl compound may also be a dialkyldiallylammonium salt such as dimethyldiallylammonium chloride. The copolymers of acrylic acid and of the latter monomer are provided under the names MERQUAT 280® and MERQUAT 295® by the company CALGON.

(2) The polymers containing units which are derived from:

a) at least one monomer chosen from acrylamides or methacrylamides substituted on the nitrogen by an alkyl radical, b) at least one acidic comonomer containing one or more reactive carboxylic groups, and c) at least one basic comonomer such as esters with primary, secondary, tertiary and quaternary amine substituents of acrylic and methacrylic acids and the product of quaternization of dimethylaminoethyl methacrylate with dimethyl or diethyl sulfate.

The N-substituted acrylamides or methacrylamides more particularly preferred according to the invention are groups whose alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide as well as the corresponding methacrylamides.

The acidic comonomers are chosen more particularly from acrylic, methacrylic, crotonic, itaconic, maleic and fumaric acids as well as the alkyl monoesters having 1 to 4 carbon atoms of maleic or fumaric anhydrides or acids.

The preferred basic comonomers are methacrylates of aminoethyl, butylaminoethyl, N,N'-dimethylaminoethyl, N-tert-butylaminoethyl.

Particularly used are the copolymers whose CTFA name (4th ed. 1991) is Octylacrylamide/acrylates/butylaminoethylmethacrylate copolymer such as the products sold under the name AMPHOMER® or LOVOCRYL 47® by the company NATIONAL STARCH.

(3) The partially or completely alkylated and crosslinked polyaminoamides derived from polyaminoamides of general formula:

in which $R_{19}$ represents a divalent radical derived from a saturated dicarboxylic acid, a mono- or dicarboxylic aliphatic acid with ethylenic double bond, an ester of a lower alkanol having 1 to 6 carbon atoms of these acids or a radical which is derived from the addition of any one of said acids with a bis-primary or bis-secondary amine, and Z denotes a radical of a bis-primary, mono- or bis-secondary polyalkylene-polyamine and preferably represents:

a) in the proportions of 60 to 100 mol %, the radical

where x=2 and p=2 or 3, or alternatively x=3 and p=2
this radical being derived from diethylenetriamine, triethylenetetraamine or dipropylenetriamine;

b) in the proportions of 0 to 40 mol %, the radical (XI) above, in which x=2 and p=1 and which is derived from ethylenediamine, or the radical which is derived from piperazine:

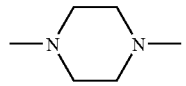

c) in the proportions of 0 to 20 mol %, the radical —NH—$(CH_2)_6$—NH— which is derived from hexamethylenediamine, these polyaminoamines being crosslinked by adding a bifunctional crosslinking agent chosen from the epihalohydrins, diepoxides, dianhydrides, diunsaturated derivatives, by means of 0.025 to 0.35 mol of crosslinking agent per amine group of the polyaminoamide and alkylated by the action of acrylic acid, chloroacetic acid or of an alkanesultone or of their salts.

The saturated carboxylic acids are preferably chosen from the acids having 6 to 10 carbon atoms such as adipic, 2,2,4-trimethyladipic and 2,4,4-trimethyladipic acid, terephthalic acid, the acids with an ethylene double bond such as for example acrylic, methacrylic and itaconic acids.

The alkanesultones used in the alkylation are preferably propane or butanesultone, the salts of the alkylating agents are preferably the sodium or potassium salts.

4) The polymers containing zwitterionic units of formula:

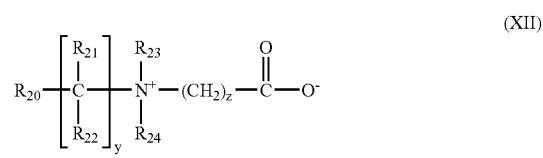

in which $R_{20}$ denotes a polymerizable unsaturated group such as an acrylate, methacrylate, acrylamide or methacrylamide group, y and z represent an integer from 1 to 3, $R_{21}$, and $R_{22}$ represent a hydrogen atom, methyl, ethyl or propyl, $R_{23}$ and $R_{24}$ represent a hydrogen atom or an alkyl radical such that the sum of the carbon atoms in $R_{23}$ and $R_{24}$ does not exceed 10.

The polymers comprising such units may also comprise units derived from nonzwitterionic monomers such as dimethyl or diethylaminoethyl acrylate or methacrylate or alkyl acrylates or methacrylates, acrylamides or methacrylamides or vinyl acetate.

By way of example, there may be mentioned the copolymer of butyl methacrylate/dimethylcarboxymethylammonioethyl methacrylate such as the product sold under the name DIAFORMER Z301® by the company SANDOZ.

(5) The polymers derived from chitosan which are described in particular in French Patents No. 2137684 or U.S. Pat. No. 3,879,376, containing monomeric units corresponding to the following formulae (XIII), (XIV), (XV) combined in their chain:

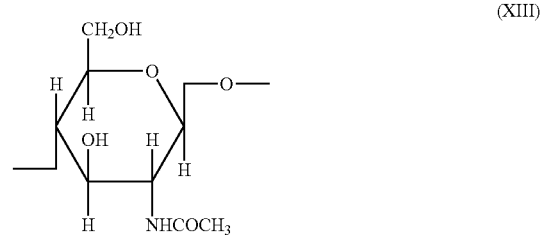

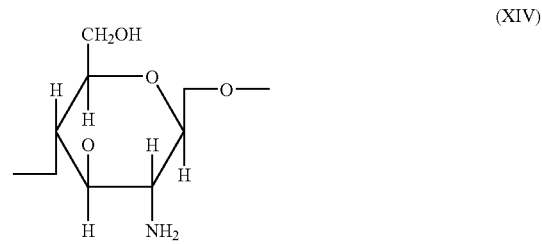

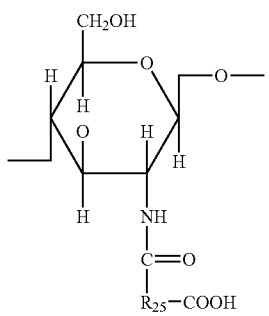 (XV)

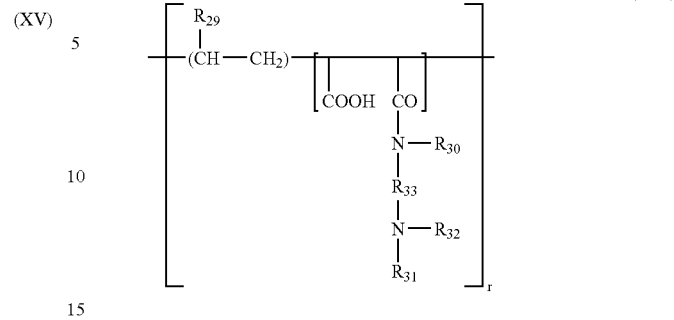 (XVI)

the (XIII) unit being present in proportions of between 0 and 30%, the (XIV) unit in proportions of between 5 and 50% and the (XV) unit in proportions of between 30 and 90%, it being understood that in this (XV) unit, $R_{25}$ represents a radical of formula:

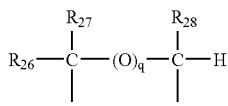

in which q denotes zero or 1;

if q=0, $R_{26}$, $R_{27}$ and $R_{28}$, which are identical or different, each represent a hydrogen atom, a methyl, hydroxyl, acetoxy or amino residue, a monoalkylamine residue or a dialkylamine residue optionally interrupted by one or more nitrogen atoms and/or optionally substituted with one or more amine, hydroxyl, carboxyl, alkylthio or sulfonic groups, or an alkylthio residue whose alkyl group carries an amino residue, at least one of the $R_{26}$, $R_{27}$ and $R_{28}$ radicals being in this case a hydrogen atom;

or if q=1, $R_{26}$, $R_{27}$ and $R_{28}$ each represent a hydrogen atom, as well as the salts formed by these compounds with bases or acids.

Polymers of this type which are more particularly preferred contain from 0 to 20% by weight of units (XIII), from 40 to 50% by weight of units (XIV), and from 40 to 50% by weight of units (XV) in which $R_{25}$ denotes the radical —$CH_2$—$CH_2$—;

(6) The polymers derived from the N-carboxyalkylation of chitosan such as N-carboxymethyl chitosan or N-carboxybutyl chitosan sold under the name "EVALSAN®" by the company JAN DEKKER.

(7) The polymers corresponding to the general formula (XI) such as those described for example in French Patent 1,400,366:

in which $R_{29}$ represents a hydrogen atom, a $CH_3O$, $CH_3CH_2O$ or phenyl radical, $R_{30}$ denotes hydrogen or a lower alkyl radical such as methyl or ethyl, $R_{31}$ denotes hydrogen or a lower alkyl radical such as methyl or ethyl, $R_{32}$ denotes a lower alkyl radical such as methyl or ethyl or a radical corresponding to the formula: —$R_{33}$—$N(R_{31})_2$, $R_{33}$ representing a group —$CH_2$—$CH_2$—, —$CH_2$—$CH_2$—$CH_2$— or —$CH_2$—$CH(CH_3)$—, $R_3$, having the meanings mentioned above, as well as the higher homolog of these radicals and containing up to 6 carbon atoms, r is such that the molecular weight is between 500 and 6 000 000, and preferably between 1000 and 1 000 000.

(8) Amphoteric polymers of the —D—X—D—X— type chosen from:

a) the polymers obtained by the action of chloroacetic acid or sodium chloroacetate on the compounds containing at least one unit of formula:

 (XVII)

where D denotes a radical

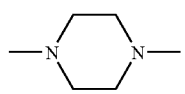

and X denotes the symbol E or E', E or E', which are identical or different, denote a bivalent radical which is an alkylene radical with a linear or branched chain containing up to 7 carbon atoms in the principal chain which is unsubstituted or substituted with hydroxyl groups and which may contain, in addition, oxygen, nitrogen or sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, or hydroxyl, benzylamine, amine oxide, quaternary ammonium, amide, imide, alcohol, ester and/or urethane groups;

b) the polymers of formula:

 (XVIII)

where D denotes a radical

and X denotes the symbol E or E' and at least once E'; E having the meaning indicated above and E' is a bivalent radical which is an alkylene radical with a linear or branched chain having up to 7 carbon atoms in the principal chain, which is unsubstituted or substituted with one or more hydroxyl radicals and containing one or more nitrogen atoms, the nitrogen atom being substituted with an alkyl chain optionally interrupted by an oxygen atom and necessarily containing one or more carboxyl functional groups or one or more hydroxyl functional groups and betainized by reaction with chloroacetic acid or sodium chloroacetate.

(9) The copolymers $(C_1-C_5)$alkyl vinyl ether/maleic anhydride partially modified by semiamidation with an N,N-dialkylaminoalkylamine such as N,N-dimethylaminopropylamine or by semiesterification with an N,N-dialkanolamine. These copolymers may also contain other vinyl comonomers such as vinylcaprolactam.

Among all the amphoteric polymers which can be used in the context of the present invention, it is preferable to use the polymers of the family (1), and in particular the copolymers of acrylic acid and dimethyldiallylammonium chloride.

According to the invention, the cationic or amphoteric polymer(s) differing from the cationic or amphoteric associative polymers may represent about 0.01% to 10% by weight, preferably 0.05% to 5% by weight, and still more preferably 0.1% to 3% by weight, of the total weight of the composition.

The dye composition may also comprise an effective quantity of other agents, which are moreover already known in oxidation dyeing, such as various customary adjuvants such as sequestrants such as EDTA, etidronic acid, UV-screening agents, waxes, volatile or nonvolatile silicones which are cyclic or linear or branched, organomodified (in particular with amine groups) or otherwise, preservatives, ceramides, pseudoceramides, vegetable, mineral or synthetic oils, vitamins or provitamins such as panthenol, opacifiers, and the like.

Said composition may also comprise reducing agents or antioxidants. These may be chosen in particular from sodium metabisulfite, thioglycolic acid, thiolactic acid, sodium bisulfite, dehydroascorbic acid, hydroquinone, 2-methylhydroquinone, tert-butylhydroquinone and homogentisic acid, and they are then generally present in quantities ranging from about 0.05 to 3% by weight relative to the total weight of the composition.

Said composition may also comprise other agents for adjusting the rheology, such as cellulosic thickeners (hydroxyethylcellulose, hydroxypropylcellulose, carboxymethylcellulose, and the like), guar gum and its derivatives (hydroxypropylguar, and the like), gums of microbial origin (xanthan gum, scleroglucan gum, and the like), synthetic thickeners such as crosslinked homopolymers of acrylic acid or acrylamidopropanesulfonic acid.

These supplementary thickeners may represent from 0.01 to 10% by weight of the total weight of the composition.

Of course, persons skilled in the art will be careful to choose the possible additional compound(s) mentioned above so that the advantageous properties intrinsically attached to the composition according to the invention are not, or not substantially, impaired by the addition(s) envisaged.

The dyeing method according to the invention preferably consists in applying a mixture, freshly prepared at the time of use from the dye composition according to the invention and an oxidizing composition, to dry or wet keratinous fibers, and in allowing it to act for a leave-in time preferably varying from 1 to 60 minutes approximately, and more preferably from 5 to 45 minutes approximately, in rinsing the fibers, and then optionally in washing them with shampoo, and then in rinsing them again, and in drying them.

In the oxidizing composition, the oxidizing agent is preferably chosen from urea peroxide, alkali metal bromates or ferricyanides, persalts such as perborates and persulfates. The use of hydrogen peroxide is particularly preferred. This oxidizing agent advantageously consists of a solution of hydrogen peroxide whose titer may vary more particularly from about 1 to 40 volumes, and still more preferably from about 5 to 40.

It is also possible to use, as oxidizing agent, one or more oxidoreduction enzymes such as oxidoreductases containing 4 electrons (such as laccases), peroxidases and oxidoreductases containing 2 electrons (such as uricase), where appropriate in the presence of their respective donor or cofactor.

The pH of the composition applied to the keratinous fibers [composition resulting from mixing the dye composition according to the invention and the oxidizing composition], is generally between the values 3 and 12. It is preferably between 6 and 11, and may be adjusted to the desired value by means of acidifying or alkalinizing agents well known in the state of the art for dyeing keratinous fibers.

Among the alkalinizing agents, there may be mentioned, by way of example, aqueous ammonia, alkali metal carbonates, alkanolamines such as mono-, di- and triethanolamines and their derivatives, sodium or potassium hydroxides and compounds of the following formula (VI):

in which R is a propylene residue optionally substituted with a hydroxyl group or a $C_1-C_4$ alkyl radical; $R_{11}$, $R_{12}$, $R_{13}$ and $R_{14}$, which are identical or different, represent a hydrogen atom, a $C_1-C_4$ alkyl or $C_1-C_4$ hydroxyalkyl radical.

The acidifying agents are conventionally, by way of example, inorganic or organic acids such as hydrochloric acid, orthophosphoric acid, carboxylic acids such as tartaric acid, citric acid, lactic acid, or sulfonic acids.

Concrete examples illustrating the invention will now be given without, however, being limiting.

EXAMPLES

The following dye composition in accordance with the invention was prepared:

| | |
|---|---|
| Mixture of C18 to C24 linear alcohols [C18/C20/C22/C24: 7/58/30/6 - alcohol content >95%] | 3 |
| Mixture of oxyethylenated C18 to C24 linear alcohols | 1 |

-continued

| | |
|---|---|
| [C18/C20/C22/C24: 7/58/30/6 - alcohol content >95%] (30 EO) | |
| Oxyethylenated stearyl alcohol (2 EO) | 4.5 |
| Oxyethylenated stearyl alcohol (21 EO) | 1.75 |
| Crosslinked polyacrylic acid (Carbopol 980 from GOODRICH) | 0.6 |
| Oleic acid | 2.6 |
| Aculyn 44 or Aculyn 46 from the company ROHM & HAAS | 4 |
| Monoisopropanolamide of copra acids | 3 |
| Cationic polymer W according to the invention | 4 AS* |
| Glycerine | 5 |
| Hexylene glycol | 1 |
| Sodium metabisulfite | 0.71 |
| EDTA (ethylenediaminetetraacetic acid) | 0.2 |
| tert-Butylhydroquinone | 0.3 |
| 1,4-Diaminobenzene | 0.2 |
| Para-aminophenol | 1.2 |
| 1,3-Dihydroxybenzene | 0.1 |
| 1-Hydroxy-3-aminobenzene | 0.2 |
| 1-Methyl-2-hydroxy-4-β-hydroxyethylaminobenzene | 0.8 |
| Monoethanolamine | 1 |
| Aqueous ammonia containing 20% of $NH_3$ | 11 |
| Perfume . . . qs | |
| Demineralized water . . . qs | 100 |

(expressed in grams)
AS* denotes Active Substance

Oxidizing Composition:

| | |
|---|---|
| Fatty alcohol | 2.3 |
| Oxyethylenated fatty alcohol | 0.6 |
| Fatty amide | 0.9 |
| Glycerin | 0.5 |
| Hydrogen peroxide | 7.5 |
| Perfume | qs |
| Demineralized water . . . qs | 100 |

Said dye composition was mixed, at the time of use, in a plastic bowl with the oxidizing composition given above, in an amount of 1 part of dye composition per 1.5 parts of oxidizing composition.

The mixture obtained was applied to locks of natural hair which was 90% white and left in for 30 minutes.

The locks were then rinsed with water, they were washed with standard shampoo and again rinsed with water, and then dried and disentangled.

The hair was dyed in a coppery red light chestnut brown shade, which was chromatic and resistant, and the cosmetic condition of the hair was improved.

Identical results were obtained by replacing, in the above dye composition, the hexylene glycol with the same quantity of 1,5-pentanediol.

The invention claimed is:

1. A composition for the oxidation dyeing of keratinous fibers, comprising, in an appropriate medium for dyeing, at least one oxidation dye, at least one $C_{12}$–$C_{30}$ fatty alcohol and at least one oxyalkylenated or polyglycerolated $C_{12}$–$C_{30}$ fatty alcohol; wherein it additionally comprises 2 to 15% by weight of a mixture of glycerine (A) and of a polyol different from glycerine (B) in an (A)/(B) weight ratio >1.

2. The composition as claimed in claim 1, wherein the mixture of glycerine (A) and polyol different from glycerine (B) is present in concentrations of between 5 and 10% by weight relative to the total weight of the composition.

3. The composition as claimed in claim 1, wherein the polyol different from glycerine is a diol.

4. The composition as claimed in claim 3, wherein the diol is hexylene glycol.

5. The composition as claimed in claim 1, wherein the glycerine is present in concentrations between 1.5 and 14% by weight relative to the total weight of the composition.

6. The composition as claimed in claim 1, wherein the polyol(s) different from glycerine are present in concentrations between 0.5 and 7% by weight relative to the total weight of the composition.

7. The composition as claimed in claim 1, wherein the $C_{12}$–$C_{30}$ fatty alcohol(s) are present in concentrations between 0.1 and 15% by weight relative to the total weight of the composition.

8. The composition as claimed in claim 7, wherein the $C_{12}$–$C_{30}$ fatty alcohol(s) are present in concentrations between 0.5 and 10% by weight relative to the total weight of the composition.

9. The composition as claimed in claim 1, wherein the oxyalkylenated or polyglycerolated $C_{12}$–$C_{30}$ fatty alcohol(s) are present in concentrations between 0.1 and 15% by weight relative to the total weight of the composition.

10. The composition as claimed in claim 9, wherein the oxyalkylenated or polyglycerolated $C_{12}$–$C_{30}$ fatty alcohol(s) are present in concentrations between 0.5 and 10% by weight relative to the total weight of the composition.

11. The composition as claimed in claim 1, wherein the oxidation dye(s) are chosen from oxidation bases and/or couplers.

12. The composition as claimed in claim 1, wherein it comprises at least one oxidation base.

13. The composition as claimed in claim 12, wherein the oxidation bases are selected from the group consisting of ortho- or para-phenylenediamines, double bases, ortho- or para-aminophenols, and heterocyclic bases, and the addition salts of these compounds with an acid, and are present in concentrations ranging from 0.0005 to 12% by weight relative to the total weight of the composition.

14. The composition as claimed in claim 11, wherein the composition comprises coupler(s) selected from the group consisting of meta-aminophenols, meta-phenylenediamines, meta-diphenols, naphthols, heterocyclic couplers, and the addition salts of these compounds with an acid, and are present in concentrations ranging from 0.0001 to 15% by weight relative to the total weight of the composition.

15. The composition as claimed in claim 13, wherein the addition salts with an acid of the oxidation dyes (bases and couplers) are selected from the group consisting of hydrochlorides, hydrobromides, sulfates, tartrates, lactates and acetates.

16. The composition as claimed in claim 1, wherein it further comprises at least one direct dye in the proportion of 0.001 to 20% by weight relative to the total weight of the composition.

17. The composition as claimed in claim 1, wherein the appropriate medium for dyeing is an aqueous medium or a water and organic solvent medium different from (A) and from (B).

18. The composition as claimed in claim 17, wherein the organic solvents different from (A) and from (B) are present in concentrations ranging from 0.5 to 20% by weight relative to the total weight of the composition.

19. The composition as claimed in claim 1, wherein it comprises at least one anionic, nonionic, cationic or amphoteric associative polymer.

20. The composition as claimed in claim 19, wherein the associative polymer(s) are nonionic and are chosen from polyether-polyurethanes.

21. The composition as claimed in claim 20, wherein the polyether-polyurethane is a polycondensate of polyethylene glycol containing 150 or 180 mol of ethylene oxide, stearyl alcohol and at least one diisocyanate.

22. The composition as claimed in claim 21, wherein it is a polycondensate of polyethylene glycol comprising 150 or 180 mol of ethylene oxide, stearyl alcohol and methylenebis (4-cyclohexyl isocyanate), at 15% by weight in a matrix of maltodextrin (4%) and water (81%).

23. The composition as claimed in claim 20, wherein the polyether-polyurethane is a polycondensate of polyethylene glycol comprising 150 or 180 mol of ethylene oxide, decyl alcohol and at least one diisocyanate.

24. The composition as claimed in claim 23, wherein the polyether-polyurethane is a polycondensate of polyethylene glycol comprising 150 or 180 mol of ethylene oxide, decyl alcohol and methylenebis(4-cyclohexyl isocyanate), at 35% by weight in a mixture of propylene glycol (39%) and water (26%).

25. The composition as claimed in claim 19, wherein the associative polymer(s) are present in the proportion of 0.1 to 10% by weight relative to the total weight of the composition.

26. The composition as claimed in claim 19, wherein it further comprises at least one cationic or amphoteric polymer different from the anionic, nonionic, cationic or amphoteric associative polymers.

27. The composition as claimed in claim 26, wherein the cationic or amphoteric polymer is selected from the group consisting of:

1/the homopolymers of dimethyldiallylammonium chloride;

2/the polymers containing the repeating units of the following formulae (W) or (U):

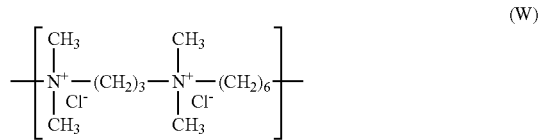

(W)

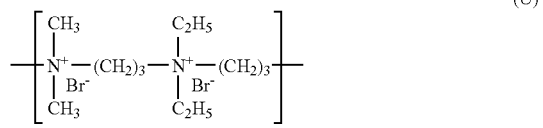

(U)

3/the polymers containing the units of the following formula (IX):

28. The composition as claimed in claim 26, wherein said cationic or amphoteric polymer(s) are present in the proportion of 0.01 to 10% by weight relative to the total weight of the composition.

29. The composition as claimed in claim 1, wherein it comprises at least one surfactant different from the oxyalkylenated or polyglycerolated $C_{12}$–$C_{30}$ fatty alcohols selected from anionic, cationic, nonionic, amphoteric or zwitterionic surfactants in the proportion of at least 0.01 % by weight relative to the total weight of the composition.

30. A method for the dyeing of keratinous fibers comprising:

applying to the fibers at least one dye composition as defined in claim 1, the color being developed at alkaline, neutral or acidic pH, using an oxidizing composition comprising at least one oxidizing agent which is mixed just at the time of use with the dye composition or which is sequentially applied with no intermediate rinsing.

31. The method as claimed in claim 30, wherein the oxidizing agent is selected from hydrogen peroxide, urea peroxide, alkali metal bromates or ferricyanides, persalts, and oxidoreduction enzymes with optionally their respective donor or cofactor.

32. The method as claimed in claim 31, wherein the oxidizing agent is in a solution of hydrogen peroxide whose titer varies from 1 to 40 volumes.

33. The method as claimed in claim 30, wherein the pH is between 6 and 11.

34. The method as claimed in claim 30, comprising applying the composition, freshly prepared at the time of use from the dye and oxidizing compositions, to dry or wet keratinous fibers, allowing it to act for a leave-in time varying from 1 to 60 minutes approximately, rinsing the fibers, and optionally washing them with shampoo, and then rinsing them again, and drying them.

35. A two-compartment device or kit for dyeing keratinous fibers wherein the first compartment contains a dye composition as defined in claim 1, and the second compartment contains an oxidizing composition.

36. The composition of claim 1, wherein the keratinous fibers are human keratinous fibers.

37. The method for the dyeing of keratinous fibers of claim 30, wherein the keratinous fibers are human keratinous fibers.

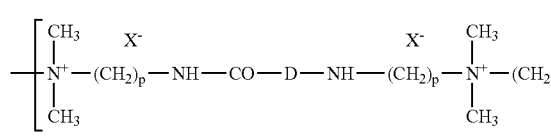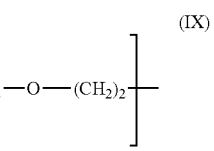

(IX)

a) D denotes the value zero, X denotes a chlorine atom, b) D represents a group —(CH$_2$)$_4$—CO—, X denotes a chlorine atom, c) D represents a group —(CH$_2$)$_7$—CO—, X denotes a chlorine atom

, d) a "Block Copolymer" consisting of units corresponding to the polymers described in paragraphs a) and b); and 4/the copolymers of acrylic acid and dimethyldiallylanimonium chloride.

38. The two-compartment device or kit for dyeing keratinous fibers of claim 35, wherein the keratinous fibers are human keratinous fibers.

39. The composition of claim 1, wherein the keratinous fibers are hair.

40. The method for the dyeing of keratinous fibers of claim 30, wherein the keratinous fibers are hair.

41. The two-compartment device or kit for dyeing keratinous fibers of claim 35, wherein the keratinous fibers are hair.

* * * * *

UNITED STATES PATENT AND TRADEMARK OFFICE
CERTIFICATE OF CORRECTION

PATENT NO. : 7,198,649 B2
APPLICATION NO. : 10/432603
DATED : April 3, 2007
INVENTOR(S) : Francois Cottard et al.

Page 1 of 1

It is certified that error appears in the above-identified patent and that said Letters Patent is hereby corrected as shown below:

Column 32, line 45, "hydrochiorides" should read --hydrochlorides--.

Column 33, line 55, after the formula, please add --for which p is equal to 3, and,--;

line 61, "atom" should read --atom,--;

line 62, delete ",".

Signed and Sealed this

Seventh Day of August, 2007

JON W. DUDAS
*Director of the United States Patent and Trademark Office*